(12) United States Patent
Smith et al.

(10) Patent No.: US 6,423,730 B1
(45) Date of Patent: Jul. 23, 2002

(54) METHOD TO CONTROL TERMITES

(75) Inventors: Frisby Davis Smith, North Wales; Ricky Hunter, Philadelphia, both of PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 3 days.

(21) Appl. No.: 09/717,853

(22) Filed: Nov. 21, 2000

Related U.S. Application Data

(60) Provisional application No. 60/171,046, filed on Dec. 16, 1999.

(51) Int. Cl.[7] ............................................... A01N 43/78
(52) U.S. Cl. ....................................................... 514/365
(58) Field of Search .......................................... 514/365

(56) References Cited

U.S. PATENT DOCUMENTS 5,045,554 A    9/1991    Alt et al. .................... 514/365

*Primary Examiner*—Allen J. Robinson
(74) *Attorney, Agent, or Firm*—Thomas D. Rogerson; Carl D. Corvin

(57) ABSTRACT

The present invention relates to a method for controlling termites by treating the termites or the locus wherein the termites live, with a 5-carboxanilido-bis-trifluoromethyl-thiazole fungicide. This invention also relates to a method for controlling the damage caused by termites and to termite damage resistant articles.

9 Claims, No Drawings

METHOD TO CONTROL TERMITES

This application claims the benefit of U.S. provisional application No. 60/171,046, filed Dec. 16, 1999.

The present invention relates to a method for controlling termites by treating the termites or the locus wherein the termites live, with a 5-carboxanilido-bis-trifluoromethyl-thiazole fungicide. This invention also relates to a method for controlling the damage caused by termites and to termite damage resistant articles.

The wood protection industry requires products that provide protection against wood destroying insects, especially termites. In the United States alone the annual damage caused by termites is placed at approximately US$ 1.4 Billion. Presently, the most effective agents for controlling termites or the damage caused by termites are based upon copper-chrome-arsenic (CCA) or insecticides such as chlorpyrifos, synthetic pyrethroids, and aldrin. However, these materials do not have the combination of biological and physicochemical properties necessary for effective termite control (residual activity against termites combined with acceptable environmental effects and low mammalian toxicity). Therefore, there is continuing need for new materials which can be used to control termites and which do not possess the unwanted characteristics of currently used materials.

U.S. Pat. No. 5,045,554 discloses a class of substituted 5-carboxanilidothiazoles useful for control of plant fungus disease such as, for example Basidiomycetes such as Rhizoctonia, Sclerotium, and Corticium, as well as Alternaria and Spirothica, when applied to the growing plant, preferably as a foliar spray. Such 5-carboxanilidothiazoles are not known to have significant insecticidal activity. We have discovered that certain of these 5-carboxanilidothiazoles are surprisingly effective as termiticides.

The present invention provides a method for controlling termites comprising applying to termites or to a locus of the termites a termiticidaly effective amount of a composition comprising one or more compounds of Formula I:

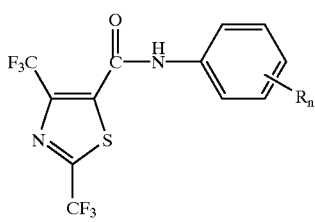

and salts thereof;
wherein: each R is independently halo (preferably chloro, bromo, or iodo), halo($C_1$–$C_5$)alkyl (preferably halo ($C_1$–$C_2$)alkyl, more preferably perhalomethyl, most preferably trifluoromethyl), halo($C_1$–$C_5$)alkoxy (preferably halo($C_1$–$C_2$)alkoxy, more preferably perhalomethoxy, most preferably trifluoromethoxy), nitro, cyano, pentahalosulfur (preferably pentafluorosulfur), halomethylthio, haloethylthio, ($C_1$–$C_2$)alkylsulfinyl, halo($C_1$–$C_2$)alkylsulfinyl, ($C_1$–$C_2$)alkylsulfonyl, or halo($C_1$–$C_2$)alkylsulfonyl; n is from two to five (preferably two to four, more preferably three to four, most preferably three). Salts of the compound of Formula I include salts of strong bases, preferably a salt from reaction with sodium or potassium hydroxide, diazabicycloundecene, or diazabicyclononane, more preferably a salt formed from reaction with sodium or potassium hydroxide. Preferably each R is independently halo, haloalkyl, or haloalkoxy. Preferably, at least one, more preferably at least two, of the R groups are located in the ortho and/or para positions.

The term "locus" means the environment in which termites are found or the environment in which the compound of Formula I may be released such that it subsequently comes into contact with termites. Such loci include, for example, timber, timber-based construction, foundations and pillars of buildings, wood and wood products, soil, crops, grassland, forests (trees and fallen logs), cellulose and cellulose-based materials, termite nests, coating materials for wires and cables, and the like. The term "termiticidaly effective amount" means the quantity of compound which provides a desired level of termite control.

The term "carboxanilido" means $C_6H_5$—NH—CO—.
The term "alkyl" means straight or branched chain ($C_1$–$C_5$) alkyl, unless otherwise specified. The term "substituted aryl" means an aryl group having one or more of its hydrogens replaced with another substituent group.

The term "lipophilic" means having an affinity for organic solvents rather than aqueous solvents.

The term "active ingredient" means a compound of Formula I and/or any other compound with pesticidal activity.

As used herein, all percentages are percent by weight, unless otherwise specified. All percentage ranges are inclusive. All ratios are by weight and all ratio ranges are inclusive.

Another embodiment this invention provides a method to control termite damage comprising applying to a locus of termites a termiticidaly effective amount of a composition comprising one or more compounds of Formula I as described above. A third embodiment of this invention provides articles of manufacture which are resistant to termite damage.

The advantage of the use of a compound of Formula I as a termiticide lies in its efficacy at low treatment rates and its non-repellent effect on termites. Known methods for termite treatment necessitate the use of relatively large amounts of a termiticide to create a physical barrier of relatively high chemical concentration sufficient to kill some of the termites and deter others from immediately reinfesting the treated locus. The present invention effectively eliminates termite populations by allowing a large number of termites to actually visit, contact, and carry away a small but efficacious amount of the termiticidal compound of Formula I.

The compounds of Formula I can be applied to various loci such as the soil, any wood or cellulose-based material, or an area visited or occupied by termites. For such purposes these compounds can be used in the technical or pure form as prepared or as formulated compositions. Solid compositions include, for example: wettable powders typically containing, for example, from 10 to 90%, preferably from 50 to 90% active ingredient, from 2 to 10% dispersing agents, up to 10% stabilizers and/or other additives such as penetrants, stickers, and surfactants, and a solid inert carrier such as clay, silica, or natural or synthetic carrier; dusts which are usually formulated as a concentrate having a composition similar to a wettable powder but without dispersant and usually containing from 0.5 to 10% active ingredient; granules containing, for example, from 0.01 to 80% active ingredient and 0 to 10% additives such as stabilizers, surfactants, slow release modifiers, and binding agents which are prepared by, for example, agglomeration or impregnation techniques and have a size greater than wettable powders and up to 1–2 millimeters; and baits containing, for example, from 0.01 to 25% active ingredient prepared by combining the active ingredient with a cellulose-based material and other additives. Liquid compositions include, for example, aqueous or solvent based solutions, emulsifiable concentrates, emulsions, suspension concentrates, and flowables which typically contain from 0.01 to 99.9% of the active ingredient, an acceptable carrier, and one or more adjuvants. More typically such liquid compositions will contain from 1.0 to 85% of the active ingredient.

As used herein, the term "carrier" means any material with which the compound of Formula I is formulated to facilitate application to the locus or to facilitate storage, transport, or handling of the compound of Formula I. A carrier may be a solid or liquid, including a material which is normally gaseous but which has been compressed to form a liquid. Any of the carriers typically useable in formulating insecticidal compositions may be used. Suitable solid carriers include, for example, natural and synthetic clays and silicates, salts such as calcium carbonate and ammonium sulfate, carbon-based materials such as charcoal and bitumen, sulfur, natural and synthetic resins, waxes, agar, fertilizers, cellulose-based materials such as sawdust and corn cobs, and mixtures thereof. Suitable liquid carriers include, for example, water, alcohols, ketones, ethers, aromatic and aliphatic hydrocarbons, petroleum fractions, chlorinated hydrocarbons, polar organic liquids, and mixtures thereof. Combinations of solid and liquid carriers may also be used.

It is usually desirable, particularly in the case of sprayable formulations, to include one or more adjuvants, such as wetting agents, spreading agents, dispersing agents, stickers, adhesives, emulsifying agents and the like in accordance with agricultural practices. Such adjuvants commonly used in the art can be found in *McCutcheon's Emulsifiers and Detergents, McCutcheon's Emulsifiers and Detergents/Functional Materials*, and *McCutcheon's Functional Materials* all published annually by McCutcheon Division of MC Publishing Company (New Jersey) and *Farm Chemicals Handbook* published by Meister Publishing Company (Ohio).

Termiticidal compositions may also contain other ingredients, for example, further active compounds possessing herbicidal, insecticidal, or fungicidal properties, in accordance with the requirements of the locus to be treated and the treatment method.

The method of applying a compound of Formula I to combat termites comprises applying the compound, in the form of a composition as described above, to a locus or area to be treated for the termites, such as, for example, soil or timber, already subject to infestation or attack by termites or intended to be protected from infestation by termites. The active ingredient is applied in an amount sufficient to effect the desired action of combating termite infestation. This dosage is dependent upon many factors including, for example, the carrier employed, the method and conditions of the application, whether the composition is present at the locus in the form of a film or as discrete particles such as a bait, the thickness of film or size of particles, and the degree of termite infestation. In general, the effective dosage of the compound of Formula I at the locus to be protected is of the order of 0.001 to 1.0% based on the total weight of the composition. Under some circumstances, readily determined by those skilled in the art, the effective dosage may be as low as 0.0001% or as high as 2% on the same basis.

The compounds of Formula I may be used to combat termites in the soil, thereby achieving indirect protection of any timber-based construction erected on the treated soil or to crops, grassland, forestry, and other cellulose-based materials surrounded by or located in or on the treated soil. Suitable soil-based control of termites is obtained by providing in the soil a termiticidaly effective amount of a compound of Formula I. For use in this manner, the active ingredient is suitably broadcast onto the soil surface or applied under the soil surface at a rate of from 0.01 grams to 10 kilograms per hectare. In addition to the compositions described above, for this use, the compound of Formula I can be formulated as a compound impregnated wooden stake. In addition to broadcast applications, the compositions of Formula I can be applied by band, furrow, or side-dress techniques or as soil drench, with or without subsequent incorporation.

Compounds of Formula I may also be applied directly on or into a material to be protected from termite damage. Such materials or articles of manufacture are then resistant to termite damage. For example, timber may be treated before, during, or after it is incorporated into a structure or building, thereby protecting it against damage for termites or combating an already existing termite infestation. For timber treatment, the compound of Formula I composition may optionally contain a penetrant, such as, for example, parafinic hydrocarbons, 2-ethoxyethanol, or methyl isobutyl ketone, and/or an anti-bloom agent, such as, for example, dibutyl phthalate or o-dichlorobenzene. Timber treatment compositions may also optionally contain fungicides, other insecticides, and/or pigments. For such applications, the compound of Formula I or its composition may be incorporated into a coating, such as, for example, a paint, stain, or natural wood colorant which is applied to the surface of the timber.

Application onto or into wood or timber may be accomplished using conventional techniques such as immersion of the timber into a liquid composition, painting by spraying or brushing, dipping, or injecting the composition into the timber. For such applications, the concentration of the compound of Formula I in the composition should be sufficient to provide an effective amount of the compound in or on the timber.

Wood or timber may also be impregnated with the compound of Formula I using well know procedures such as, for example, pressure treatments such as the Lowery empty cell process and full cell process, vacuum treatment, hot and cold bath treatment, thermal treatment, and cold-soak treatment.

Compounds of Formula I are prepared by standard procedures as disclosed in U.S. Pat. No. 5,045,554 (see particularly columns 4–15) by reacting a 2,4-bis-tribluoromethyl substituted thiazole having a 5-carbonylchloride substituent with an appropriately substituted aniline in suitable solvent(s) at an elevated temperature. For example:

Preparation of 2,4-bis-trifluoromethylthiazole-5-carboxylic acid chloride

Step 1—Preparation of Trifluorothioacetamide

To a 1 L 4-neck round bottom flask (RBF), equipped with a mechanical stirrer, nitrogen inlet, addition funnel and thermometer, was charged trifluoroacetamide (56.0 grams (g), 1.0 equiv. 0.495 mole) and 100 g of Lawesson's reagent followed by 500 milliliters (mL) of tetrahydrofuran. The reaction mixture was heated to boiling for 2 hours. The solvent was carefully removed by rotary evaporation to yield 86 g of crude product. This material was distilled by kugelrohr distillation under high vacuum (<1 mm Hg) to afford 54 g of light yellow liquid trifluorothioacetamide (84% yield).

Step 2—Preparation of Ethyl Chlorotrifluoroacetoacetate

To a 500 mL 3-neck RBF equipped with a magnetic stirrer, nitrogen inlet, thermometer and gas bubbler was charged 200 g of ethyl trifluoroacetoacetate. Using an acetone/ice bath the reaction vessel was cooled to 0–10° C. and at this temperature chlorine gas was added to the reaction vessel via a gas bubbler at sufficient rate to maintain the reaction from 5 to 15° C. Chlorine gas was added until a yellow color persisted in the reaction mixture. The reaction solution was allowed to warm to room temperature and then heated to 30° C. while gas was evolved. When the gas evolution stopped, the resulting mixture provided 226 g of product (95% yield).

Step 3—Preparation of ethyl 2,4-bis-trifluoromethyl-5-thiazole carboxylate

To a 3 L 4-neck RBF equipped with a mechanical stirrer, reflux condenser, thermometer and addition funnel was charged 358 g of ethyl chlorotrifluoroacetoacetate (1.64 moles), 2,2,2-trifluorothioacetamide and 1000 mL of acetonitrile. To this mixture was added 331.9 g of triethylamine (2.0 eq, 3.28 moles) dropwise over 2.5 hours. During the addition the temperature was maintained at 30–38° C. and upon completion of the addition the reaction was heated to reflux for 2 hours and stirred overnight at room temperature. The reaction mixture was filtered and the resulting filtrate was concentrated by rotary evaporation to provide an oily solid which was dissolved in 1500 mL of ethyl acetate. This was washed with 2×500 mL of water, 1×500 mL of brine and concentrated by rotary evaporation to yield 356.6 g of ethyl 2,4-bis-trifluoromethyl-5-thiazole carboxylate which was purified by distillation.

Step 4—Preparation of 2,4-bis-trifluoromethylthiazole-5-carboxylic acid

To a 1 L 4-neck RBF was charged ethyl 2,4-bis-trifluoromethyl-5-thiazole carboxylate (23.8 g, 1.0 equiv., 81.2 mmole) in 100 mL THF and 50 mL water. The reaction mixture was cooled to 20° C. and 10% NaOH solution (32.5 g, 1.0 equiv., 81.2 mmole) was added. The ice-bath was removed after 5 minutes and the mixture was stirred for 4 hours. After reaction was complete, as determined by thin layer chromatography, 100 mL ether and 100 mL water were added. The aqueous phase was separated and acidified with conc. HCl, extracted with ether, and the ether was removed by rotary evaporation to give a solid which was washed with water and vacuum filtered. The solid was dried in a vacuum oven to give 16.5 g (76.7% yield) product as a brown solid, mp=98–101° C.

Step 5—Preparation of 2,4-bis-trifluoromethylthiazole-5-carboxylic acid chloride To a 500 mL 1-neck RBF under $N_2$ was added 2,4-bis-trifluoromethylthiazole-5-carboxylic acid (31.5 g, 1.0 equiv., 0.119 moles) in 25 mL chloroform and 1 mL dimethylformamide (DMF). To this solution was added thionyl chloride (28.3 g, 2.0 equiv., 0.24 moles). The reaction was then heated at reflux for 6 hours. The reaction was cooled to room temperature and concentrated by rotary evaporation at 30° C. to remove solvent. Chloroform was added, 3×25 mL portions, concentrating by rotary evaporation each time, to give 29.8 g (88.4% yield) product as a brown oil.

Aniline Coupling Reactions

Prep. of Compound 1—N-(2,4,6-trichlorophenyl)-2,4-bis-trifluoromethylthiazole-5-carboxanilide To a 250 mL 1-neck RBF under nitrogen was added 2,4-bis-trifluoromethyl-thiazole-5-carboxylic acid chloride (25.8 g, 1.0 equiv., 91.0 mmoles) in 30 mL toluene and then 2,4,6-trichloroaniline (17.9 g, 1.0 equiv., 91.0 mmoles). The mixture was heated at reflux for 6 hours with monitoring by gas-liquid liquid chromatography (GLC). Upon completion the reaction was cooled to room temperature. A dark colored solid formed upon cooling after residual toluene was evaporated. The dark colored solid was washed with methylene chloride, vacuum filtered, and further washed with hexanes to give 33.2 g (82.2% yield) product as an off-white solid, mp=180–182° C.

Preparation of Compound 2—2'-bromo-4',6'-dichloro-2,4-bis-trifluoromethyl-1,3-thiazole-5-carboxanilide To a 125 mL 1-neck flask under nitrogen was added 1.0 g (1.0 eq., 3.5 mmole) of 2,4-bis-trifluoromethyl-1,3-thiazole-5-carboxylic acid chloride and 0.85 g (1.0 eq., 3.5 mmole) of 2-bromo-4,6-dichloroaniline in 10 mL toluene. The mixture was heated at reflux for 6 hours. The mixture was cooled and the solvent was removed leaving a solid residue. The residue was triturated with lene chloride followed by a hexane wash to give 1.1 g product as a white/pink solid (mp=179–182° C., 63.9% yield) (NMR ($^1$H, 300 MHz: 7.5(d, 1H); 7.6(d, 1H); 7.7(s, 1H)).

The following compounds were prepared in a similar manner:

| Cmpd # | $R_n$ | Melting Point ° C. | NMR $^1$H, 300 MHz |
|---|---|---|---|
| 3 | 4-Br-2,6-di-Cl | 191–194 | 7.6(s, 2H); 7.7(s, 1H) |
| 4 | 3,4,5-tri-Cl | 179–182 | 7.7(s, 2H); 7.9(s, 1H) |
| 5 | 2,6-di-Br-4-OCF$_3$ | 167–168.5 | 7.57(s, 2H); 7.7(s, 1H) |
| 6 | 2,3,4-tri-Cl | 132–134 | 7.49(m, 1H); 8.35(m, 1H); 8.46 (s, 1H) |
| 7 | 2,4,5-tri-Cl | 153–155 | 7.55(s, 1H); 8.4(s, 1H); 8.64(s, 1H) |
| 8 | 2,4-di-Cl | 122–125 | 7.35(m, 1H); 7.47(m, 1H); 8.37 (d, 2H) |
| 9 | 2,5-di-Cl | 142–144 | 7.17(m, 1H); 7.39(d, 1H); 8.48 (d, 2H) |
| 10 | 2,6-di-Cl | 181–183 | 7.29(m, 1H); 7.44(d, 2H); 7.7(s, 1H) |
| 11 | 3,5-di-Cl | 175–178 | 7.26(s, 1H); 7.53(d, 2H); 7.9(s, 1H) |

EXAMPLE 1

Compounds of Formula I were evaluated using standard evaluation methodology as prescribed by the American Wood Preservers Association Standard AWPA E1-97, incorporated herein by reference, using a species of the destructive termite, Reticulitermes.

In this test replicate containers containing damp sand and southern yellow pine wood blocks treated with the compound are used. Termites are introduced into the test container and after four weeks the containers are disassembled and the wood blocks are evaluated for termite damage. Termite mortality is also evaluated.

The results of this evaluation are as follows:

| Compound # | End Use Level (kg/m$^3$) | Minimum Retention (kg/m$^3$) Preventing Termite Attack |
|---|---|---|
| 1 | 0.080 | 0.400 |
| 5 | 0.384 | 0.768 |
| Comparative* | 0.288 | >0.160 |

*= chlorpyrifos
kg/m$^3$ = kilograms per cubic meter

EXAMPLE 2

Subterranean worker termites, *Reticulitermes lalvipes*, were purchased from Carolina Biological Supply Co. The insects were stored with their shipping material, decayed wood chips and moist paper towels, in an unlit growth chamber at 13° C. for three days prior to start of the test. This delay was to acclimate the termites to the test conditions as well as to eliminate weak individuals.

The compounds tested, 100 mg each, were dissolved in 10 mL of pure ethanol (dehydrated, 200 proof) to provide a solution of 10,000 ppm. The solution was serial diluted by 10× to achieve dilutions of 1,000, 100, 10, and 1 ppm. A pure cellulose fiber filter pad was soaked with 1 mL of each test sample and placed into a Falcon petri dish (50×9 mm sterile polystyrene). In addition, a pine wood chip, approximately 12×12×4 mm was dipped into the test solution for 30 seconds and placed on the filter paper. Solvent from the treated filters and wood chips was then allowed to evaporate for 24 hours. The next day, five termites were placed on the filter pad and the upper lid of the petri plate was secured. Three replications were used for each treatment.

The termites in the petri dishes were returned to the growth chamber at 13° C. The humidity was high enough to allow for condensation on the upper plate surface, which provided water for the termites. The petri dishes were briefly removed from the chamber at 2, 4, and 8 days after treatment to count the number of live termites. Data was expressed as the percentage of control (kill) of termites.

The results of this evaluation are as follows:

| Cmpd #→ | Control (% kill at 8 days) | | | | | | | |
|---|---|---|---|---|---|---|---|---|
| Dose (ppm) ↓ | 8 | 9 | 10 | 11 | 6 | 7 | 4 | 1 |
| 10,000 | 100 | 100 | 73 | 67 | 100 | 100 | 100 | 100 |
| 1,000 | 20 | 53 | 67 | 13 | 100 | 100 | 73 | 93 |
| 100 | 0 | 20 | 0 | 13 | 53 | 87 | 33 | 100 |
| 10 | 0 | 40 | 0 | 7 | 27 | 60 | 47 | 87 |
| 1 | 7 | 27 | 7 | 0 | 33 | 73 | 77 | 93 |

These data indicate that the trisubstituted compounds show activity superior to that of the disubstituted compounds. The data also indicate that substitution at the ortho and para positions of the phenyl ring provides optimum activity.

We claim:

1. A method for controlling termites, wherein said method comprises applying to said termites, or to a locus infested with said termites, a termiticidaly effective amount of a composition comprising one or more compounds, or salts thereof, of the formula

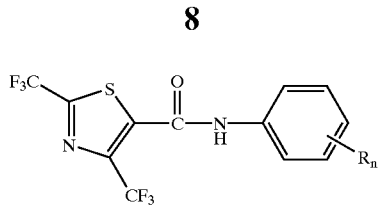

wherein each R is independently halo, halo($C_1$–$C_5$)alkyl, halo($C_1$–$C_5$)alkoxy, nitro, cyano, pentahalosulfur, halomethylthio, haloethylthio, ($C_1$–$C_2$)alkylsulfinyl, halo($C_1$–$C_2$)alkylsulfinyl, ($C_1$–$C_2$)alkylsulfonyl, or halo($C_1$–$C_2$)alkylsulfonyl and n is from two to five.

2. The method of claim 1 wherein each R is independently chloro, bromo, iodo, halo($C_1$–$C_2$)alkyl, or halo($C_1$–$C_2$)alkoxy and n is from three to four.

3. The method of claim 2 wherein each R is independently chloro, bromo, trifluoromethyl, or trifluoromethoxy, n is three, and the R groups are in the ortho and para positions.

4. The method of claim 3 wherein each R is chloro.

5. A method for controlling termite damage, wherein said method comprises applying to a locus infested with termites a termiticidaly effective amount of a composition comprising one or more compounds, or salts thereof, of the formula wherein each R is independently halo, halo($C_1$–$C_5$)alkyl, halo($C_1$–$C_5$)alkoxy, nitro, cyano, pentahalosulfur, halomethylthio, haloethylthio, ($C_1$–$C_2$)alkylsulfinyl, halo($C_1$–$C_2$)alkylsulfinyl, ($C_1$–$C_2$)alkylsulfonyl, or halo($C_1$–$C_2$)alkylsulfonyl and n is from two to five.

6. The method of claim 5 wherein each R is independently chloro, bromo, iodo, halo($C_1$–$C_2$)alkyl, or halo($C_1$–$C_2$)alkoxy and n is from three to four.

7. The method of claim 6 wherein each R is independently chloro, bromo, trifluoromethyl, or trifluoromethoxy, n is three, and the R groups are in the ortho and para positions.

8. The method of claim 7 wherein each R is chloro.

9. The method of claim 1 or claim 5 wherein said locus is selected from the group consisting of timber, timber-based construction, foundations of buildings, pillars of buildings, wood, wood products, soil, crops, grassland, forests, cellulose, cellulose-based materials, termite nests, or coating materials for wires and cables.

* * * * *